(12) United States Patent
Nakazawa et al.

(10) Patent No.: US 9,335,238 B2
(45) Date of Patent: May 10, 2016

(54) DEVICE FOR FORMING TISSUE PIECES FOR TISSUE ARRAY

(75) Inventors: Yoshiaki Nakazawa, Nagano (JP); Masaki Takano, Nagano (JP); Masahiko Arakawa, Nagano (JP); Kohji Naritake, Nagano (JP)

(73) Assignees: Sakura Seiki Co., Ltd., Nagano (JP); Sakura Finetek Japan Co., Ltd., Nagano (JP)

( * ) Notice: Subject to any disclaimer, the term of this patent is extended or adjusted under 35 U.S.C. 154(b) by 90 days.

(21) Appl. No.: 13/810,660

(22) PCT Filed: Jul. 26, 2011

(86) PCT No.: PCT/JP2011/066975
§ 371 (c)(1),
(2), (4) Date: Jan. 16, 2013

(87) PCT Pub. No.: WO2012/014896
PCT Pub. Date: Feb. 2, 2012

(65) Prior Publication Data
US 2013/0122540 A1    May 16, 2013

(30) Foreign Application Priority Data
Jul. 29, 2010    (JP) .................................. 2010-170954

(51) Int. Cl.
*G01N 1/30* (2006.01)
*G01N 1/28* (2006.01)
*G01N 1/36* (2006.01)
*C12M 1/33* (2006.01)

(52) U.S. Cl.
CPC ................. *G01N 1/30* (2013.01); *C12M 45/02* (2013.01); *G01N 1/286* (2013.01); *G01N 1/36* (2013.01)

(58) Field of Classification Search
None
See application file for complete search history.

(56) References Cited

U.S. PATENT DOCUMENTS 7,503,245 B2 * 3/2009 Miyazawa et al. ................. 83/13
7,811,518 B2 * 10/2010 Kokubo .......................... 422/65

FOREIGN PATENT DOCUMENTS

| | | |
|---|---|---|
| JP | 63037918 | 2/1988 |
| JP | 63273056 | 11/1988 |
| JP | 11108928 | 4/1999 |
| JP | 11297351 | 10/1999 |
| JP | 11322445 | 11/1999 |
| JP | 20011369668 | 5/2001 |
| JP | 2001515735 | 9/2001 |
| JP | 2005175345 | 6/2005 |
| WO | WO-2008108410 | 12/2008 |
| WO | WO-2010027012 | 3/2010 |

OTHER PUBLICATIONS

Sakura Seiki Co., Ltd., et al., International Search Report for PCT/JP2011/066975 dated Sep. 20, 2011.

* cited by examiner

*Primary Examiner* — Blaine Lankford
(74) *Attorney, Agent, or Firm* — Blakely Sokoloff Taylor & Zafman LLP

(57) ABSTRACT

The invention provides a method for forming tissue pieces which allows stable and accurate winding around a core rod in rolling a sheet-like tissue piece, and a device therefor.
In the tissue pieces used as each tissue piece in a tissue array obtained by arranging the tissue pieces on a substrate in an array form, the method for forming a roll-shaped tissue piece 6 obtained by rolling a sheet-like tissue piece 8 is characterized by the facts that the sheet-like tissue piece 8 is produced by slicing a tissue block 5 obtained by embedding the tissues with an embedding medium, the sheet-like tissue piece 8 is placed on a mounting block 12, peeling means 13 which easily enables peeling of the tissue piece 8 from the mounting block 12 is applied between the mounting block 12 and the tissue piece 8, and the tissue piece 8 is wound around a core rod 11 while heating the tissue piece 8 on the mounting block 12.

10 Claims, 7 Drawing Sheets

DEVICE FOR FORMING TISSUE PIECES FOR TISSUE ARRAY

CROSS-REFERENCE TO RELATED APPLICATION

This is a non-provisional application claiming the benefit of International Patent Application No. PCT/JP2011/066975, filed Jul. 26, 2011.

TECHNICAL FIELD

The present invention relates to a method for forming tissue pieces used for manufacturing of a tissue array obtained by arranging the tissue pieces on a substrate in an array form, and a device for forming the tissue pieces.

BACKGROUND ART

For test and analysis of body tissues, a tissue array constituted by arranging a plurality of tissue pieces on a substrate is used. The tissue array is used for testing of presence or absence of lesional tissues, analysis and screening of genes and proteins, etc. by coating or the like of a staining solution which specifically stains test article, or the like.

In relation to formation of tissue pieces constituting the tissue array, it has been general to punch a tissue block embedded with an embedding medium such as paraffin and to circularly cut out the tissue block for sampling a core.

However, according to such a method for forming the tissue pieces, there have been problems in which a particularly region of interest which especially attracts attention in the lesional tissue in the tissue block may be deleted when it is slice after sampling of the core.

Furthermore, among researchers who study body tissues, some researchers think that punching the tissue block is undesirable for the subsequent researches because the region is completely deleted from the tissue block.

Therefore, there have been examined the formation of the tissue pieces constituting the tissue array, not by the method of cutting out the circular core from the tissue block, but by another method.

Methods proposed in order to solve the above-mentioned problems are disclosed in Patent Literatures 1 and 2.

In the methods for forming tissue piece disclosed in Patent Literatures 1 and 2, a tissue block is first slice by a microtome or the like and a sheet-like tissue piece is obtained. Subsequently the sheet-like tissue piece is rolled up.

The roll-shaped tissue piece is inserted into a hole of the substrate block obtained by forming an embedding medium such as paraffin into a block shape. When a predetermined number of roll-shaped tissue pieces are arranged on the substrate block, the substrate block is sliced so that the roll-shaped tissue pieces are in the form of circular slices, and the slices are placed on a substrate such as a microscope slide, for the formation of a tissue array.

In this way, in the formation methods described in Patent Literatures 1 and 2, various regions in a wide range of tissues can be put into one tissue piece by rolling the sheet-like tissue piece, and thus the problem of deleting the particularly region of interest which especially attracts attention in the lesional tissue can be solved.

Consequently, the tissue can remain only by thinly slicing its surface without punching the tissue block and can be useful for subsequent studies.

PRIOR ART DOCUMENTS

Patent Documents

PTL 1: WO 2010/027012, the brochure
PTL 2: WO 2008/108410, the brochure

DISCLOSURE OF THE INVENTION

Problems to be Solved

In the methods for forming the tissue piece described in Patent Literatures 1 and 2, when the thinly slice sheet-like tissue piece is rolled up, the sheet-like tissue piece is rolled around a core rod.

Since the tissue block itself is embedded with the embedding medium such as paraffin, the embedding medium such as paraffin softens by winding the tissue piece around the core rod while heating it, and thus flexibility at the time of winding can be improved and destruction of the tissue is avoided.

However, in a case of heating of the sheet-like tissue piece, there exists a problem in which when the tissue piece is heated on a mounting block on which the tissue piece is placed, the sheet-like tissue piece is welded to the mounting block by fusion of the embedding medium such as paraffin, and thus winding around the core rod is not possible. In order to solve such a problem, the sheet-like tissue piece has to be heated in the air, but in such a case, there exist problems in which stable and highly accurate winding cannot be expected, and the tissue piece is required to be manually wound around the core rod, and thus winding of the tissue piece around the core rod cannot be automated.

Therefore, the present invention has been made to solve the above-mentioned problems, and the object is to provide a method for forming the tissue pieces which allows stable and accurate winding around the core rod in rolling the sheet-like tissue piece, and a device therefor.

Solutions to be Solved

According to the method for forming the tissue pieces for the tissue array related to the present invention, wherein the tissue pieces are used as each tissue piece in the tissue array obtained by arranging the tissue pieces on the substrate in the array form, the method for forming the roll-shaped tissue piece obtained by rolling the sheet-like tissue piece is characterized by the fact that the sheet-like tissue piece is produced by slicing the tissue block obtained by embedding the tissues with the embedding medium, the sheet-like tissue piece is placed on the mounting block, peeling means which easily enables peeling of the tissue piece from the mounting block is applied between the mounting block and the tissue piece, and the tissue piece is wound around the core rod while heating the tissue piece on the mounting block.

Since adoption of this method easily enables its peeling from the mounting block by the peeling means even in a state where the sheet-like tissue piece is softened by heating with heating means, the tissue piece can be stably wound around the core rod with high accuracy. Because stable and highly accurate winding is possible, the winding requires no human hand and can be automated. In addition, since the sheet-like tissue piece can be wound in a softened state, the tissue piece can be wound without destruction of the tissue.

In addition, the peeling means may be characterized by coating of an embedding medium having a lower melting point than that of the embedding medium contained in the sheet-like tissue piece on the mounting block.

According to this, the embedding medium having the low melting point is melted by heating means and lies in a liquid state between the sheet-like tissue piece and the mounting block. Thereby, the sheet-like tissue piece can be easily peeled from the mounting block.

Additionally, the peeling means may be characterized by roughening of an upper face of the mounting block.

Such a method can also facilitate peeling of the sheet-like tissue piece from the mounting block.

In addition, the mounting block may be characterized by points that a mounting block having a heating table incorporating a heater and a plate detachable from an upper face of the heating table is used and wherein the peeling means is provided on an upper face of the plate.

According to this method, the sheet-like tissue piece is placed on the plate, heated and then cooled down to make a sheet-like tissue piece plate to which the sheet-like tissue piece is welded on a surface of the plate. Damage or the like of the sheet-like tissue piece can be prevented by previously making a plurality of sheet-like tissue piece plates, and thus the sheet-like tissue piece can be easily handled. In addition, information of contents of the tissues or the like (e.g. identification code) can be described on the plate, which thus contributes to prevention of mix-ups of the sheet-like tissue pieces.

Furthermore, the mounting block may be characterized by the fact that a sheet-like member having a melting point higher than that of the embedding medium contained by the sheet-like tissue piece is placed, the sheet-like tissue piece is placed on the upper face of the sheet-like member, and the tissue piece and the sheet-like member are wound around the core rod while the tissue piece is heated at a temperature to the extent that the sheet-like member on the mounting block is not fused.

According to this method, even when the sheet-like tissue piece is damaged, it can be securely wound around the core rod, and even when the melting point of the embedding medium contained by a plurality of sheet-like tissue pieces varies, it can be steadily wound around the core rod regardless of the melting point of the plurality of sheet-like tissue pieces. Furthermore, when the roll-shaped tissue piece is formed and inserted into a paraffin block or the like to thereby form a tissue array, the sheet-like tissue piece is wrapped with the sheet-like member having the high melting point, and thus the roll of the wound sheet-like tissue piece can be prevented from coming loose.

Meanwhile, the invention may be characterized by the fact that the chipped sheet-like tissue pieces are linearly arranged on the upper face of the sheet-like member in a direction of winding around the core rod, and the tissue piece and the sheet-like member are wound around the core rod while the tissue piece is heated at the temperature to the extent that the sheet-like member on the mounting block is not fused.

According to this method, even when the sheet-like tissue piece is chipped, the tissue piece can be constituted as a roll-shaped tissue piece. Additionally, the method has an advantage of being able to arrange only a part required for observation.

In addition, the invention may be characterized by the fact that a mark for positioning is formed at a position where the chipped sheet-like tissue piece on the upper face of the mounting block is to be linearly arranged in the direction of winding around the core rod.

In addition, the invention may be characterized by the fact that the embedding medium is coated on a surface of the core rod.

According to this method, adhesiveness at the time of winding enables stable winding.

Effects of the Invention

By the method and the device for forming the tissue piece for the tissue array of the present invention, the winding around the core rod in winding the sheet-like tissue piece into rolls can be performed stably with accuracy.

EMBODIMENTS OF THE INVENTION

Hereinafter, the method for forming the tissue piece for the tissue array according to the embodiment will be explained on the basis of the drawings.
(Method 1)

First, the procedure for making the tissue array using the method for forming the tissue piece in the present embodiment will be explained on the basis of FIGS. 1 to 6.

Figure 1:
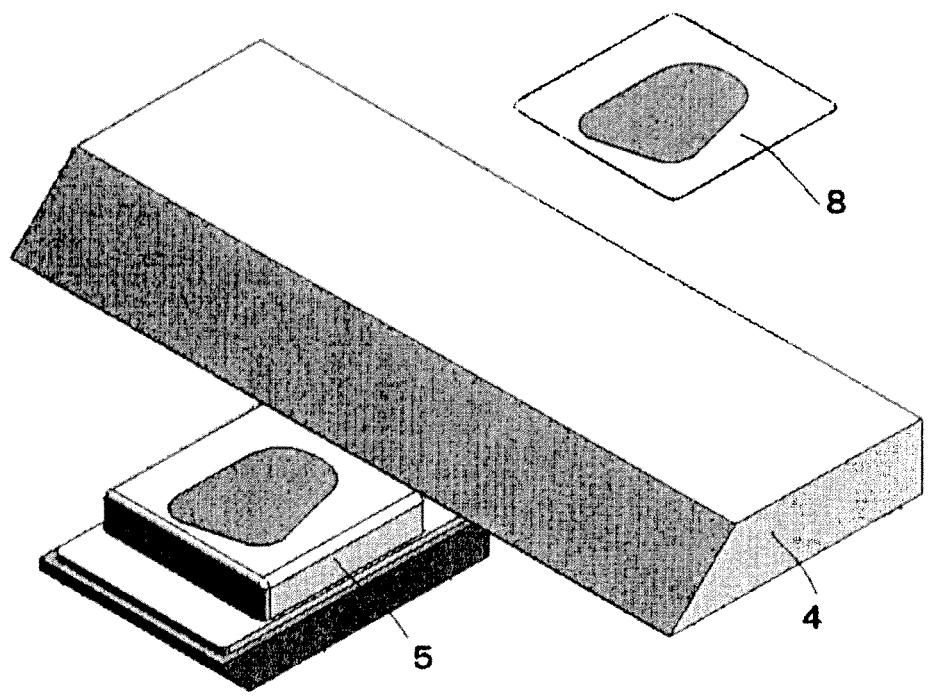
FIG. 1 illustrates an explanatory drawing of cutting out of the sheet-like tissue piece.
Figure 2:
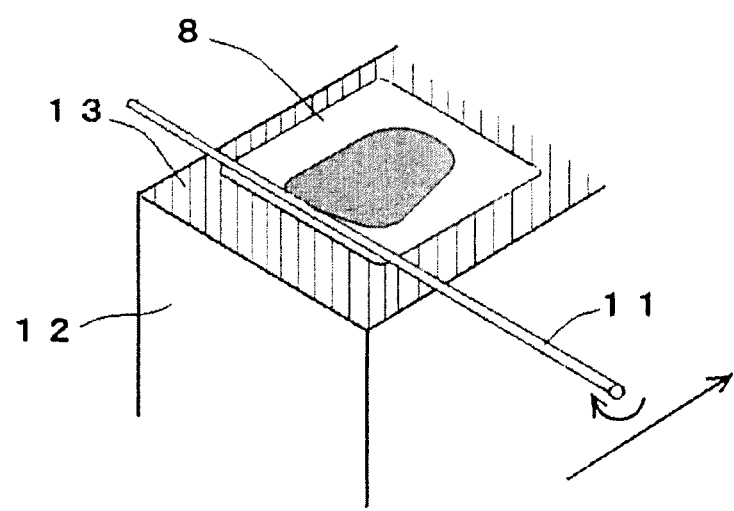
FIG. 2 illustrates an explanatory drawing of a state immediately before winding of the sheet-like tissue piece around the core rod.
Figure 3:
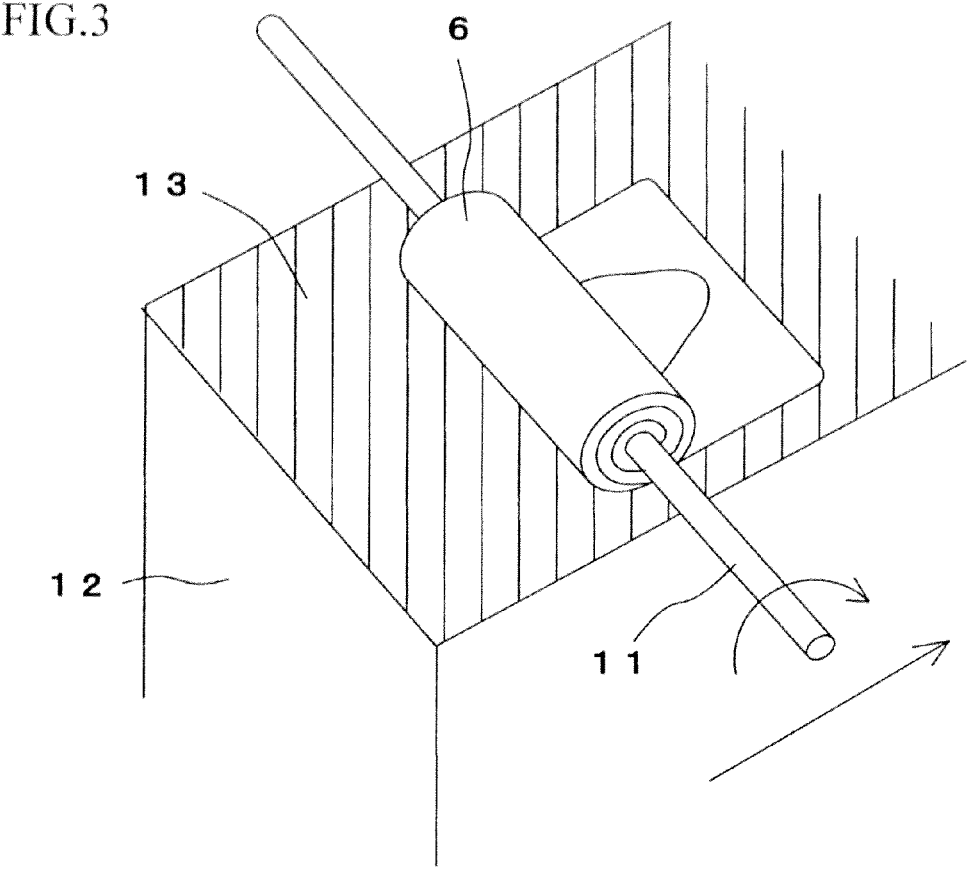
FIG. 3 illustrates an explanatory drawing of a state during winding of the sheet-like tissue piece around the core rod.

As shown in FIG. 1, a tissue block 5 embedded with the embedding medium (paraffin in the present embodiment) is cut into the shape of sheets having a thickness of approximately 100 μm by a microtome 4. The cut tissue piece having the thickness of approximately 100 μm is referred to as a sheet-like tissue piece 8.

Here, although an instrument used for slicing the tissue block 5 was exemplified by the microtome 4 herein, a vibratory microtome (not shown), laser (not shown) or another means may be used.

Next, the sheet-like tissue piece 8 is wound around the core bar and the roll-shaped tissue piece is formed.

When the sheet-like tissue piece 8 is wound around the core bar 11, the sheet-like tissue piece 8 is placed on a mounting block 12 incorporating a heater, and the sheet-like tissue piece 8 is softened by heating with the heater and then wound. The heater is exemplified by a silicon rubber heater or the like.

An embedding medium (paraffin in the embodiment) 13 having a melting point lower than that of the paraffin contained in the sheet-like tissue piece 8 is previously coated on an upper face of the mounting block 12. The paraffin having the low melting point corresponds to a peeling means in Claims. The paraffin 13 having the low melting point is fluidified through fusion by the heater on the mounting block 12, resulting in a state where the sheet-like tissue piece 8 floats on the liquid paraffin 13. This can prevent the sheet-like tissue piece 8 from being welded to the mounting block 12.

The core bar 11 is positioned on the upper face of the sheet-like tissue piece 8 placed on the mounting block 12 and is rotationally moved. Thereby, the sheet-like tissue piece 8 is wound around the core bar 11 to allow formation of the roll-shaped tissue piece 6. A cylindrical synthetic resin material is used as the core bar 11.

After the winding is completed and the roll-shaped tissue piece 6 is formed, the roll-shaped tissue piece 6 is cooled down by a cooling means or is left for natural cooling, so that a temperature of the tissue piece is lowered. Thereby, the paraffin of the roll-shaped tissue piece 6 is hardened.

Figure 4:
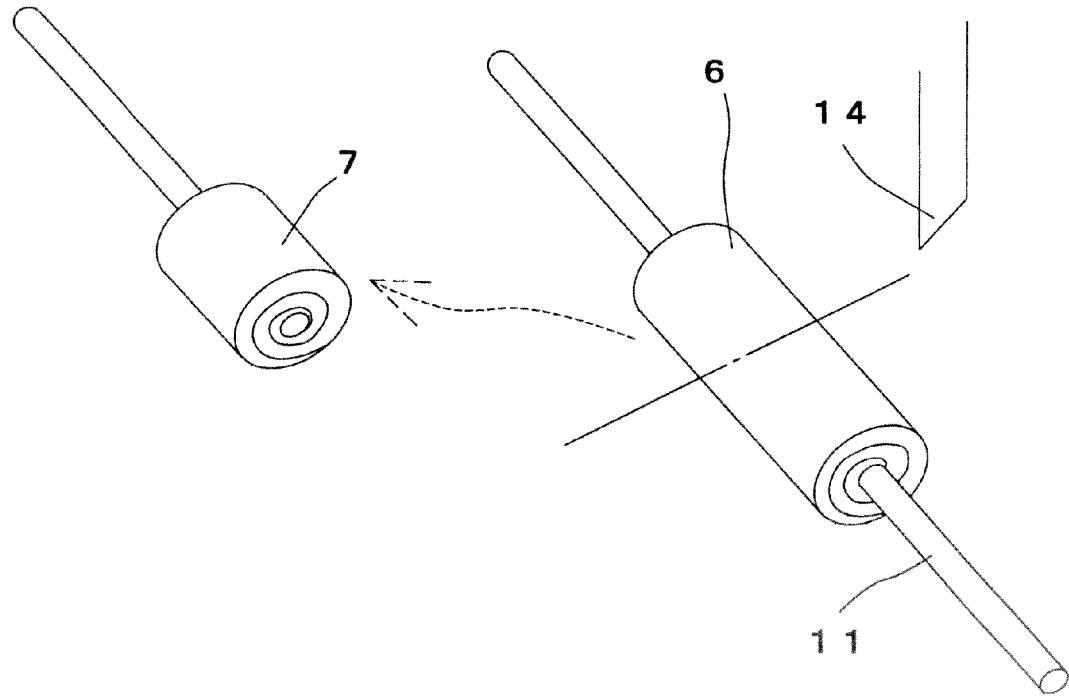
FIG. 4 illustrates an explanatory drawing of the roll-shaped tissue piece.

Next, as shown in FIG. 4, the roll-shaped tissue piece 6 is cut into a prescribed length, together with the core rod 11, so that the tissue piece 6 is in a state of being cut into cylindrical bodies. The cutting is conducted by a cutter 14. Here, the roll-shaped tissue piece 6 is cut into two pieces almost at the center of its length direction (axial direction). In any one of the two cut pieces, the core rod 11 projecting from the ends of the roll-shaped tissue piece 6 is cut out to form a roll-shaped tissue piece 7 in which the core rod 11 is unexposed. The roll-shaped tissue piece 7 in which the core rod 11 is unexposed is used in the next step.

Furthermore, since in the above-mentioned example, the core rod 11 projects from the both ends of the wound roll-shaped tissue piece 6, the projecting core rod 11 is required to be cut before the use in the next step. However, in winding the sheet-like tissue piece 8 around the core rod 11, the sheet-like tissue piece 8 may be wound so that the core rod 11 does not project from the ends of the tissue pieces. In this way, the step of cutting out the core rod 11 can be omitted.

A cylindrical material having a hollow inner space formed is preferably used as the core rod 11. In this way, when the roll-shaped tissue piece 6 is cut together with the core rod 11, the cutting is facilitated and a lifetime of the cutter 14 can be extended. The use of the core rod 11 in which a cavity is filled with an embedding medium (paraffin in the embodiment) is preferable, because the roll-shaped tissue piece 6 can be prevented from deforming by squash of the core rod 11 when the rolled tissue piece 6 is cut together with the core rod 11.

In addition, coating of the surface of the core rod 11 with the embedding medium (paraffin in the present embodiment), improves adhesiveness in winding the sheet-like tissue piece 8, and thus the stable winding can be carried out.

In this way, the core rod 11 having a surface and the cavity stuck with the paraffin can be made only by soaking the core rod 11 in the melted paraffin.

Figure 5:
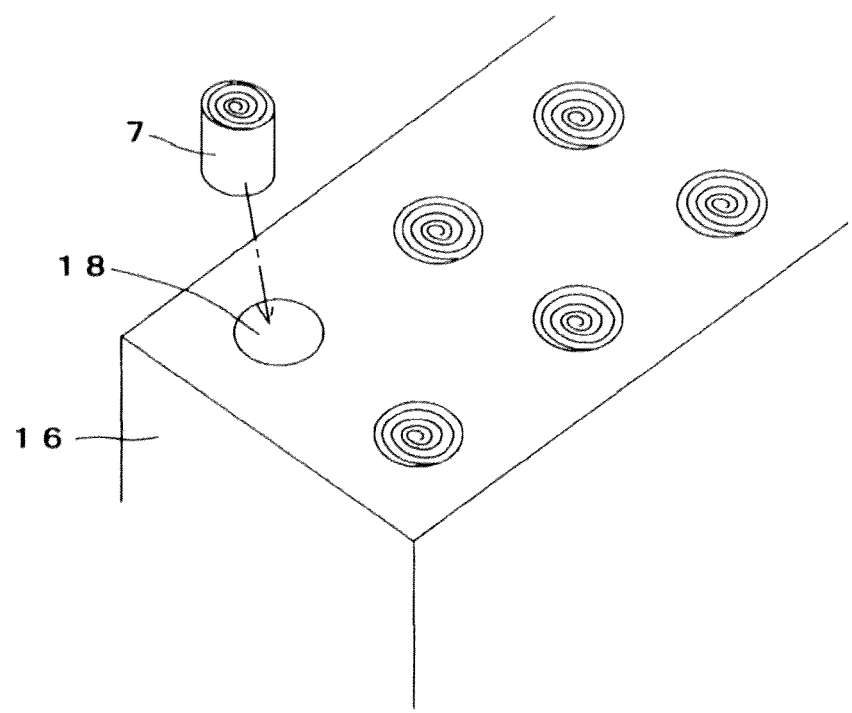
FIG. 5 illustrates an explanatory drawing of embedding of the roll-shaped tissue piece into the substrate block.

As shown in FIG. 5, the cut roll-shaped tissue pieces 7 are inserted into holes 18 of a substrate block 16 constituted by the embedding medium (paraffin in the embodiment). In the substrate block 16, a plurality of holes 18 is required to be previously made.

After the cut roll-shaped tissue pieces 7 are inserted into all of the holes 18 of the substrate block 16, the substrate block 16 is sliced in a direction in which a circular cross-section of the roll-shaped tissue piece 6 appears by a microtome (not shown) or the like.

Figure 6:
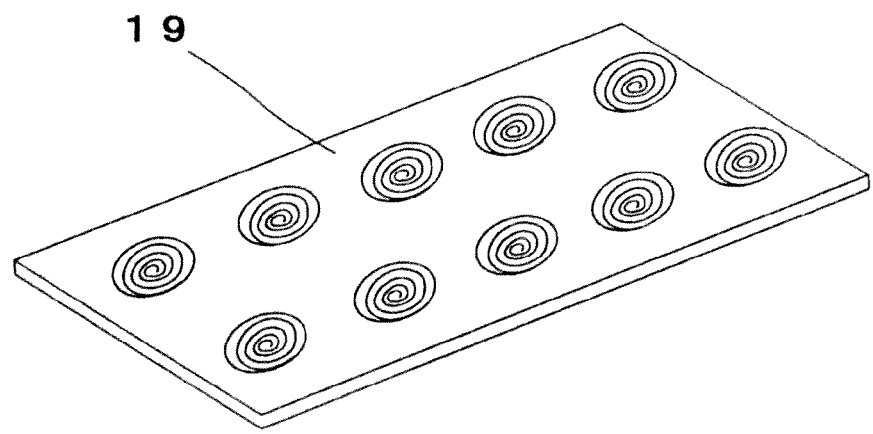
FIG. 6 illustrates a perspective view of a tissue array sheet.

As shown in FIG. 6, the sheet like material obtained by slicing the substrate block 16 is a tissue array sheet 19. Additionally, a tissue array is made by arranging the tissue array sheet 19 on the substrate. Meanwhile, it can be considered that various substrates such as a microscope slide, a nylon film substrate or a silicon substrate are used as the substrate.

It should be noted that the peeling means provided on the mounting block 12 is not limited to coating of paraffin having the low melting point.

For example, water or hot water ($H_2O$) may be dripped on the upper face of the mounting block 12. In this way, it is possible to keep the sheet-like tissue piece 8 from being welded to the upper face of the mounting block 12 because water and hot water lies between the sheet-like tissue piece 8 and the upper face of the mounting block 12. In this case, the sheet-like tissue piece 8 may curve so as to project upward by surface tension of water or hot water, but such a possibility can be avoided by adding a surfactant or the like to water or hot water. In addition, influence of surface tension of water or hot water can be reduced by performing hydrophilic treatment of the upper face of the mounting block 12. The hydrophilic treatment includes treatment such as coating of the upper face of the mounting block 12 with titanium oxide or the like.

Another example of the peeling means may include roughening of the upper face of the mounting block 12. The roughening can be achieved by giving sandblast to a surface to thereby form fine concavity and convexity on the surface.

It should be noted that roughening may be combined with the paraffin having the low melting point. That is, after the upper face of the mounting block 12 is roughened, the paraffin 13 having a melting point lower than that of the paraffin contained by the sheet-like tissue piece 8 is coated on the roughened upper face. In this way, peeling characteristics can be enhanced.

(Method 2)

A method for forming the tissue piece other than the above-mentioned method for forming the tissue piece will be explained.

It should be noted that the explanations about the slicing of the sheet-like tissue piece from the tissue block, the cutting after winding around the core rod, the insertion into the tissue block and the slicing of the tissue block are omitted.

Figure 7:
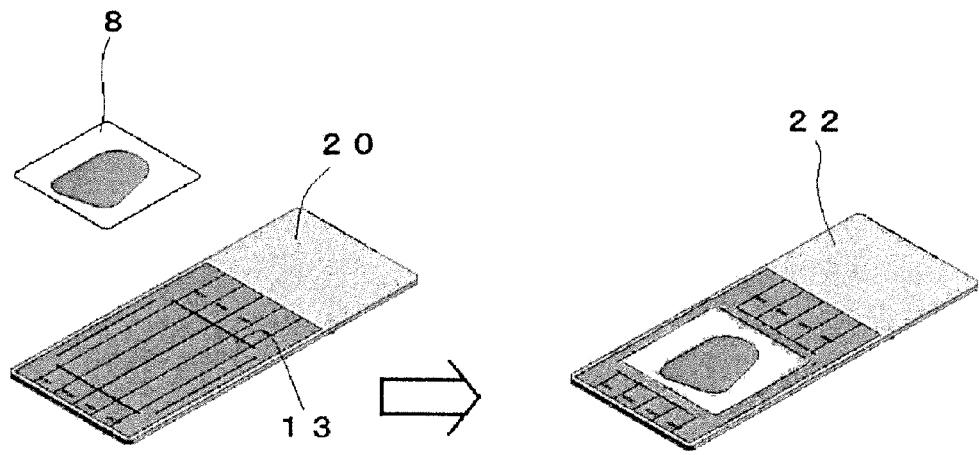
FIG. 7 illustrates an explanatory drawing of the method for forming the tissue piece by using a plate.

As shown in FIG. 7, in the present embodiment, the roll-shaped tissue block 6 is formed using a plate 20 separately from the mounting block 12 incorporating the heater. A metallic, glass or resin plate-like body can be used as the plate 20.

The upper face of the mounting block 12 is constituted so that the plate 20 is freely arranged thereon, and the plate 20 can also be heated by the heater in the mounting block 12.

Here, the peeling means 13 is provided on the upper face of the plate 20. As the peeling means, it is preferable to coat, on the upper face of the plate 20, the paraffin having a melting point lower than that of the paraffin contained by the sheet-like tissue piece 8 and to roughen the upper face of the plate 20. When the plate 20 is heated and the paraffin 13 having the low melting point is fluidized through fusion, there is reached a state where the sheet-like tissue piece 8 floats on the liquid paraffin 13. This can prevent the sheet-like tissue piece 8 from being welded to the plate 20.

In this way, by the fact that the sheet-like tissue piece 8 is placed on the plate 20 other than the mounting block 12, the following function effects are produced.

That is, the sheet-like tissue piece 8 is placed on the plate 20 and heated. Then, the sheet-like tissue piece 8 is welded to the plate 20 and a sheet-like tissue piece plate 22 is obtained. Damage of the sheet-like tissue piece 8 can be prevented by previously making a plurality of such sheet-like tissue piece plates 22. In addition, it is not possible to directly describe an identification code or the like on the sheet-like tissue piece 8, but it is possible to describe an identification code or the like on the sheet-like tissue piece plate 22. Therefore, it is also possible to prevent mix-ups of the sheet-like tissue pieces 8.

The sheet-like tissue piece plate 22 may not be necessarily made on mounting block 12 in the present embodiment and may be made on other places.

In this case, the sheet-like tissue piece plate 22 made on another plate is placed on the mounting block 12, and the sheet-like tissue piece 8 is softened by heating with a heater and then wound.

The core bar 11 is positioned on the upper face of the sheet-like tissue piece 8 placed on the mounting block 12 and is rotationally moved. Thereby, the sheet-like tissue piece 8 is wound around the core bar 11 to allow formation of the roll-shaped tissue piece 6.

(Method 3)

Subsequently, another method for forming the tissue piece will be explained.

It should be noted that the explanations about the slicing of the sheet-like tissue piece from the tissue block, the cutting after winding around the core rod, the insertion into the tissue block and the slicing of the tissue block are omitted.

Figure 8:
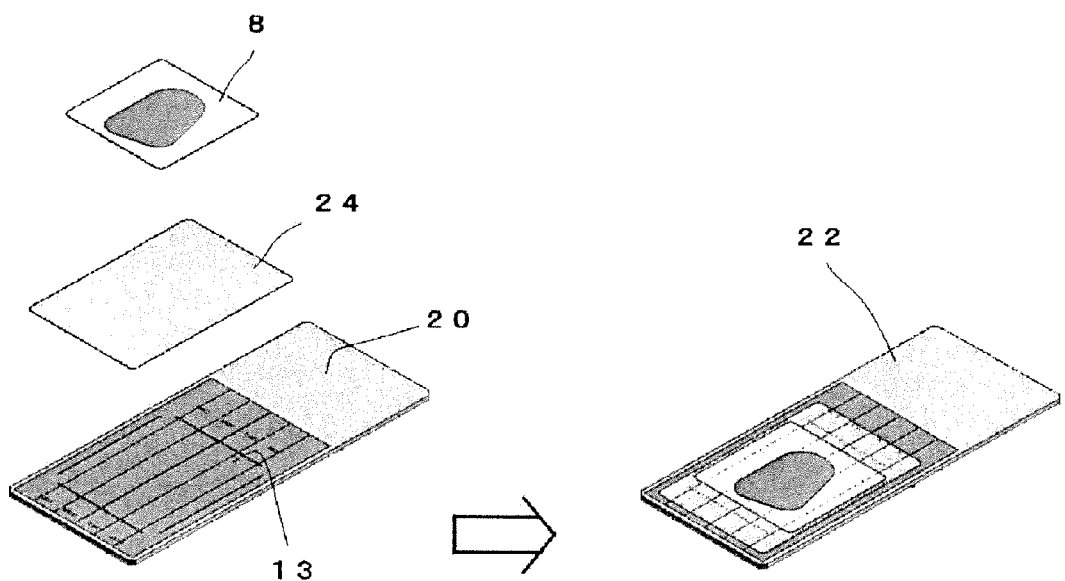
FIG. 8 illustrates an explanatory drawing of the method for forming the tissue piece by using a plate and a paraffin sheet.

As shown in FIG. 8, the present embodiment is characterized by the fact that a flexible sheet-like member is located between the plate 20 and the sheet-like tissue piece 8. The sheet-like member includes a paraffin sheet 24. This paraffin sheet 24 has a melting point higher than that of the paraffin contained by the sheet-like tissue piece 8. Furthermore, a thickness of the sheet is the same as or less than that of the sheet-like tissue piece 8. Specifically, it can be considered that the thickness is preferably 500 µm or less.

In addition, the size of the paraffin sheet 24 is required to be the same as or larger than that of the sheet-like tissue piece 8. A material of the paraffin sheet 24 may be paraffin combined with additives. The additives include butyl rubber, agarose, cellulose, microcrystalline wax, mannan, gelatin, polyethyleneglycol, silicon, EVA (ethylene-vinyl acetate copolymer), synthetic resin, mineral oil, beeswax, or the like.

When the sheet-like tissue piece 8 is wound around the core rod 11, it is wound around the core rod 11, with respect to this paraffin sheet 24.

According to this method, even if the sheet-like tissue piece 8 is damaged, it can be wound around the core rod 11.

It should be noted that the sheet-like member is not limited to the paraffin, and may be a material such as a polyamide-based member, polyisobutylene, a polyurethane-based member, a polyester-based member, polyvinyl chloride, polyethylene, a polyolefin-based member, polystyrene, polypropylene, or fluorine-based resin, or PARAFILM (trademark), HOT-MELT (trademark), MEDEL (trademark), or the like. In addition, the sheet-like member may also be a combination of a plurality of these materials.

(Method 4)

Figure 9:
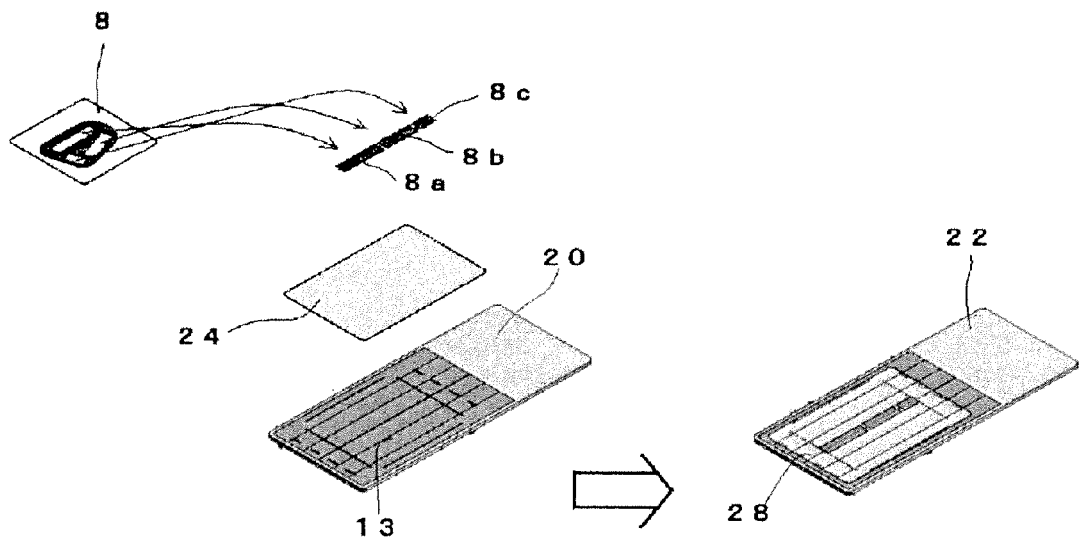
FIG. 9 illustrates an explanatory drawing of the method for forming the tissue piece, in which the tissue piece is formed by cutting out the tissue piece and linearly arranging it on the paraffin sheet.

Furthermore, as shown in FIG. 9, chipped sheet-like tissue pieces 8a, 8b, . . . are linearly arranged in a direction of winding around the core rod 11, and the sheet-like tissue piece 8 may be wound around the core rod 11 with respect to the paraffin sheet 24, while heating at a temperature to the extent that the paraffin sheet 24 on the plate 20 is not melted.

According to this method, even if the sheet-like tissue piece 8 is chipped as mentioned above, the piece 8 chipped can be constituted as the roll-shaped tissue piece 6, and among the sheet-like tissue pieces, only parts required for observation can be arranged.

When only the required parts of the tissue piece are arranged, since the arrangement of the tissue pieces is linear, there may be cases where the tissue pieces are not found, after the completion of winding, depending on a place where the tissue piece is cut in the longitudinal direction of the core rod 11.

Thus, in the plate 20, an arrangement mark 28 may preferably previously be formed at a position corresponding to the place on which the cutter 14 is positioned. The mark 28 may be any mark which is just linearly drawn.

Meanwhile, in Method 3 and Method 4 mentioned above, the cases where the paraffin sheet 24 is placed on the plate 20 have been explained.

However, in a method using the paraffin sheet 24, the use of the plate 20 is unnecessary, the paraffin sheet 24 is placed on the mounting block 12 with the upper face to which the peeling means has been applied, and the sheet-like tissue piece 8 may be arranged on the paraffin sheet 24, to thereby wind it around the core rod 11.

Each of the above-mentioned methods employ the procedure in which the tissue piece 6 is cut while the core rod 11 is held in the middle of the roll-shaped tissue piece 6, and the cut core rod 11 is also placed on the tissue array as it is. However, the core rod 11 may be pulled out from the roll-shaped tissue piece 6 after winding of the tissue piece is completed.

Meanwhile, although the embedding medium used in the present embodiment is exemplified by the paraffin, other embedding mediums include non-hydrophilic embedding mediums such as celloidin, polyester resin, polyamide resin, and (meth)acrylic acid resin, hydrophilic embedding mediums such as carbowax and gelatin, and a combination of two or more of them.

Preferable embedding mediums include paraffins such as paraffin containing an additive of a synthetic polymer such as paraffin and polyethylene.

(Device)

Hereinafter, the device for forming the tissue piece for the tissue array according to the embodiment will be explained.

It should be noted that, in relation to the same configuration used in the above-explained formation methods, the same reference numerals are used, and their explanations may be omitted.

Figure 10:
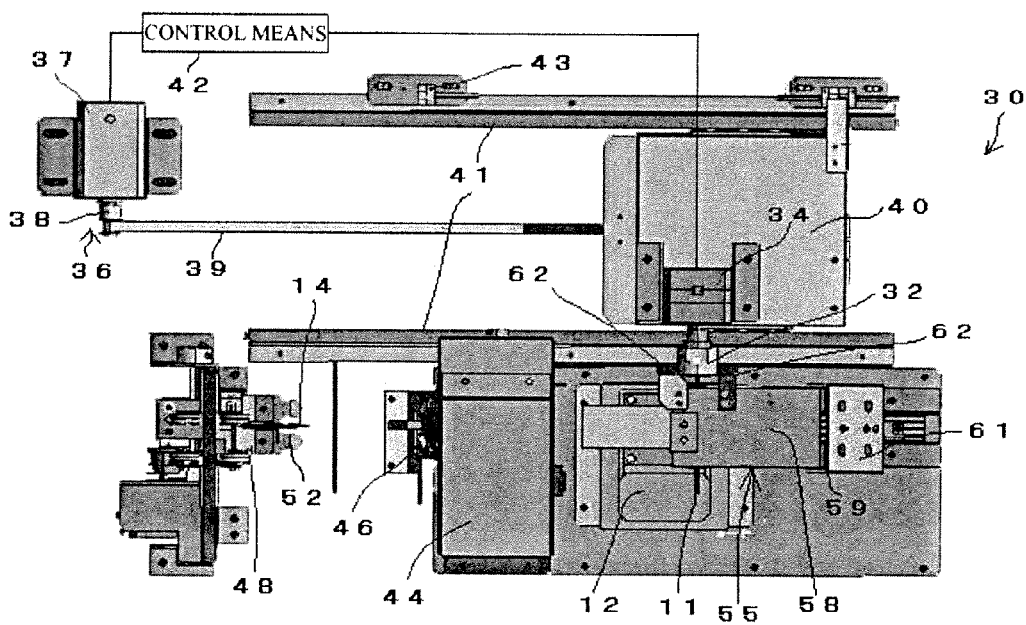
FIG. 10 illustrates a plan view of the device for forming the tissue according to the present invention.

FIG. 10 illustrates the plan view showing the overall configuration of the device for forming the tissue piece. Additionally, in a tissue piece-forming device 30, a configuration in which the plate 20 is placed on the mounting block 12 and the sheet-like tissue piece 8 arranged on the plate 20 is wound around the core bar 11 is employed.

The tissue piece-forming device 30 includes the mounting block 12 placed with the plate 20, on the upper face, on which the sheet-like tissue piece 8 composed by slicing the tissue block 5 embedded with an embedding medium such as paraffin is arranged, and the heater which heats the sheet-like tissue piece 8 placed on the plate 20 is provided in the mounting block 12.

In addition, the upper face of the plate 20 is provided with the peeling means 13, and the sheet-like tissue piece 8 can be easily peeled from the plate 20.

A core rod-attaching part 32 for attaching the core rod 11 is provided in the vicinity of the mounting block 12. In the core rod-attaching part 32, a collet chuck which inserts the core rod 11 and fixes it by fastening is used. It should be noted that the configuration of the core rod-attaching part 32 is not limited to the collet chuck.

A motor 34 which rotationally drives the core rod-attaching part 32 is connected to the rear-end portion of the core rod-attaching part 32. The core rod-attaching part 32 and the motor 34 are arranged on a movable table 40 which can move together with a belt 39.

A moving means 36 for horizontally moving this movable table 40 is provided. The moving means 36 has a motor 37, a pulley 38 provided on a rotary shaft of the motor 37, a belt 39 bridged between the pulley 38 and the movable table 40.

However, means for converting the rotary motion of the motor 37 into the linear motion for the movement of the movable table 40 is not limited to the belt driving, and may be a rack, a pinion, a ball screw, or the like. Furthermore, a straight motor provided with the means for converting the rotary motion into the linear motion may be adopted in the motor 37.

The movable table 40 is guided by two guiderails 41 extending in its moving direction, and thus linear movement is ensured.

Moreover, positioning sensors 43 for detecting a shifting position of the movable table 40 are provided on a plurality of positions in the moving direction of the movable table 40. By the fact that the positioning sensor 43 detects the movement of the movable table 40, each motion is carried out by control means 42 as mentioned below.

By the fact that the core rod-attaching part 32 horizontally moves while rotating the core rod 11, the sheet-like tissue piece 8 can be wound around the core rod 11. At this time, the control means 42 controls the driving of the motor 34 and the motor 37.

The control means 42 outputs control signals to each of the motor 34 and 37 to thereby control the rotation of each of the motor 34 an 37.

As the sheet-like tissue piece 8 is wound around the core rod 11, its diameter is gradually increased, and thus, after the start of winding, the control means 42 controls the rotation speed of the motor 34 for rotating the core rod 11 so that it is gradually decreased. In addition, after the start of winding, the control means 42 controls the rotation speed of the motor 37 for horizontally moving the core rod 11 so that it gradually increased.

By doing this, even when the diameter is gradually increased by winding, strength of winding can be maintained so that raveling is avoided.

At a downstream side of the mounting block 12 in the moving direction of the movable table 40, an adaptively heating portion (the second heating means in claims) 44 for adapting the roll-shaped tissue piece 6 wound around the core rod 11 is provided.

The adaptively heating portion 44 has a configuration in which a far-infrared heater for heating is arranged on a roof-like inner wall so as to heat the roll-shaped tissue piece 6 wound around the core rod 11 from above. However, the heater for heating may not be the far-infrared heater. In addition, it may be constituted in such a way that hot air is blown instead of providing the heater.

The roll-shaped tissue piece 6 wound around the core rod 11 which passes through the adaptively heating portion 44 is rotated by the motor 34, and thus its heating effects are evenly produced to the whole.

In addition, at a downstream side of the adaptively heating portion 44 in the moving direction of the roll-shaped tissue piece 6, a cooling portion 46 is provided for cooling the roll-shaped tissue piece 6. The cooling portion 46 is provided for cooling, to normal temperature, the roll-shaped tissue piece 6 softened by passing through the adaptively heating portion 44, to thereby harden it. This is because cutting is difficult if the tissue piece remains soft.

The cooling portion 46 in the present embodiment is provided with a fan, which cools the roll-shaped tissue piece 6 coming out of the adaptively heating portion 44, by blowing wind through the fan. However, the cooling portion 46 is not limited to this configuration.

For example, an electronic cooling method using a Peltier element or the like may be employed, and the configuration may be such that a container housing ice water is provided on the cooling portion 46, and the roll-shaped tissue piece 6 is soaked in ice water. Furthermore, the configuration may also be such that the roll-shaped tissue piece 6 passes through normal room air and a temperature of the roll-shaped tissue piece 6 is gradually cooled to room temperature.

At a downstream side of the cooling portion 46 in the moving direction of the roll-shaped tissue piece 6, a cutting device 48 is provided. The cutting device 48 is a device for cutting the roll-shaped tissue piece 6 into cylindrical bodies at a prescribed position and has the cutter 14 moving up and down.

The cutting device 48 is provided with a supporter 52 of the roll-shaped tissue piece 6 in order to support the roll-shaped tissue piece 6 in cutting. The cutter 14 is arranged almost at the center of the supporter 52.

Meanwhile, the control means 42 controls the stop of the rotary driving of the motor 37 so that horizontal movement by the motor 37 for movement is stopped at a position on which a supporter 52 is provided, and also controls the motor 34 so as to keep on rotating the core rod 11 until the cutting of the roll-shaped tissue piece by the cutting device 48 is completed.

The control means 42 performs control so that the cutting device 48 starts movement after the roll-shaped tissue piece 6 reaches the supporter 52 and the horizontal movement by the moving means 36 is stopped. The control means 42 stops the motor 37 of the moving means 36 and then lowers the cutter 14 of the cutting device 48 to thereby cut the roll-shaped tissue piece 6. When the cutter 14 is lowered and starts to cut the roll-shaped tissue piece 6, the core rod 11 and the roll-shaped tissue piece 6 bow, and thus the supporter 52 supports a lower face and any one of side faces of the roll-shaped tissue piece 6 to thereby ensure the cutting.

After the control means 42 lowers the cutter 14 to a prescribed position to thereby allow cutting of the roll-shaped tissue piece 6, the means raises the cutter to its initial position. Subsequently, the control means 42 also stops the rotation of the motor 34 which rotates the core rod 11, to thereby complete all the motions.

In this way, in the tissue piece-forming device 30 in the present embodiment, the procedures up to the cutting of the roll-shaped tissue piece 6 are automatically performed. Subsequently, the inserting steps and the like of the roll-shaped tissue piece 7 cut into the holes 18 of the substrate block 16 are manually conducted by an operator or the like.

Incidentally, the tissue piece-forming device 30 of the present embodiment is provided with pressing means 55 which presses the core rod 11 in a direction of the sheet-like tissue piece 8, when the sheet-like tissue piece 8 is wound around the core rod 11 attached to the core rod-attaching part 32.

Figure 11:
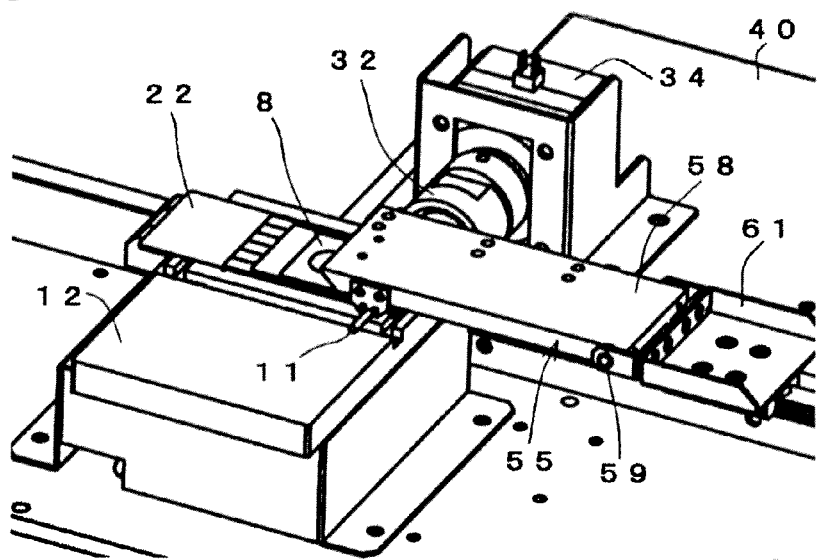
FIG. 11 illustrates an explanatory drawing of configuration of the vicinity of the mounting block.
Figure 12:
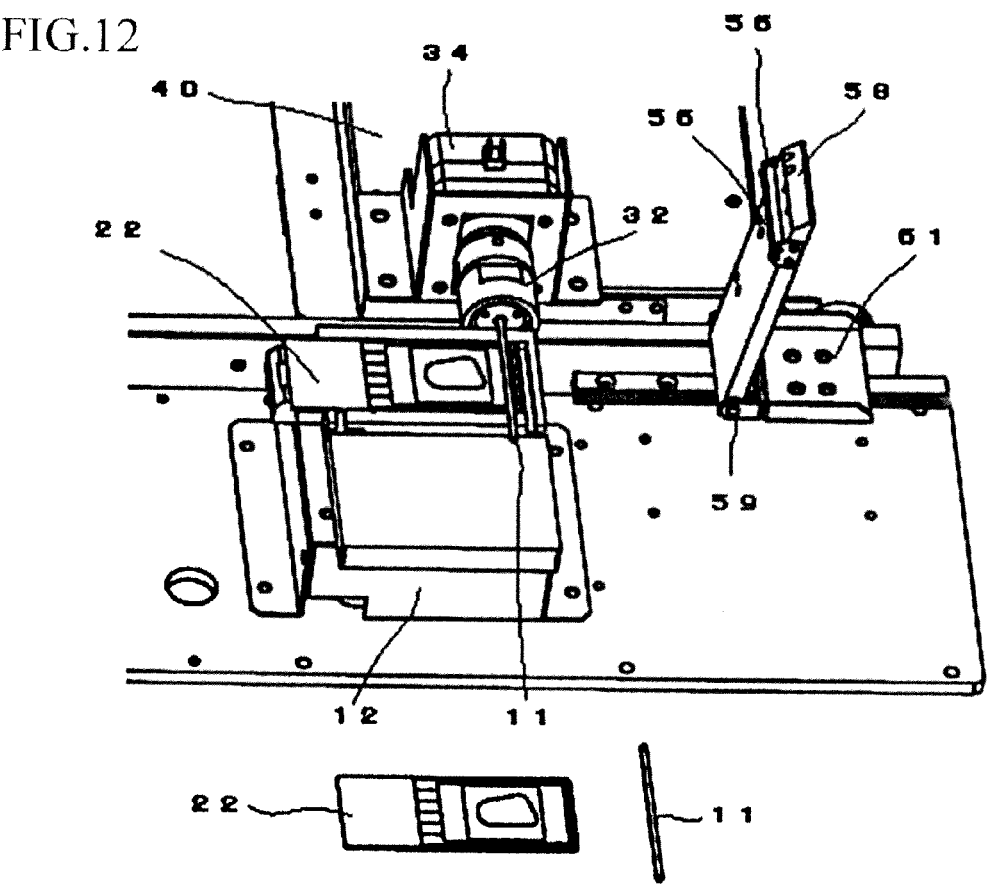
FIG. 12 illustrates an explanatory drawing of configuration of the vicinity of the mounting block in a state where a pressing plate is flipped up.

Hereinafter, the pressing means will be explained in more detail on the basis of FIGS. 11 and 12.

The pressing means 55 has a turning plate 58 comprising a freely rotatable turning shaft 59 which extends in a direction parallel to the axial direction of the core rod 11, and two holding rollers 56 and 56 which are provided in the vicinity of an end of a side (anterior end) facing a side (rear-end portion) provided with the turning shaft 59 of the turning plate 58. In the pressing means 55, its end provided with the holding rollers 56 is lowered around the freely-rotating turning shaft 59 by its own weight. The holding rollers 56 and 56 are freely rotatably provided, and they rotate together in contact with the upper face of the tissue piece to be consistently wound around the core rod 11.

In this way, the holding rollers 56 and 56 rotate together in contact with the tissue piece around the core rod 11, and thus the rotation of the core rod 11 can be performed so as not to be disturbed while pressing the core rod 11 in a direction of the tissue piece. In addition, along with the winding of the tissue piece around the core rod 11, the diameter of the tissue piece becomes gradually larger, but the turning plate 58 can gradually rise around the turning shaft 59 with the increase of the diameter of the tissue piece.

Since each of the holding rollers 56 consistently makes contact with the tissue piece, means for preventing adhesion is required to be applied so as to avoid adhesion of the tissue piece.

The means for preventing adhesion includes application or the like of a coating such as a fluorine-based resin to the surface of the holding rollers 56. In addition, effects for preventing adhesion can be produced by giving sandblast to the surfaces of the holding rollers 56 to thereby form fine concavity and convexity on the surface.

In addition, the pressing means 55 has follower means which horizontally moves along with the movement of the core rod 11 and consistently presses an upper part of the core rod 11 until the winding of the tissue piece around the core rod 11 is completed.

In the present embodiment, follower rollers 62 and 62 arranged on the both sides of the core rod-attaching part 32 are provided as the following means. The follower rollers 62 and 62 can freely rotate and are arranged so as to rotate together in contact with both sides of upstream and downstream in the moving direction of the core rod-attaching part 32. The follower rollers 62 and 62 are connected to the turning plate 58, and the follower rollers 62 and 62 can move together with the core rod-attaching part 32 to move whole the pressing means 55.

After the completion of the winding around the core rod 11, the turning plate 58 of the pressing means 55 is flipped up so that the pressing means 55 is spaced apart from the upper part of the roll-shaped tissue piece 6.

Although, as a mechanism to flip up the turning plate 58, various mechanisms can be considered, the present embodiment employs a configuration in which, by the fact that the fixation plate 61 provided on the side of rear-end portion from the turning plate 58 in the moving direction makes contact with a wall surface of the mounting block 12, the core rod-attaching part 32 advances further when the pressing means 55 reaches a position where it cannot advance any more, and thus, by the fact that the follower rollers 62 is flipped up by the core rod-attaching part 32, the turning plate 58 turns around the turning shaft 59 to thereby be spaced apart from the upper face of the roll-shaped tissue piece 6.

Figure 13:
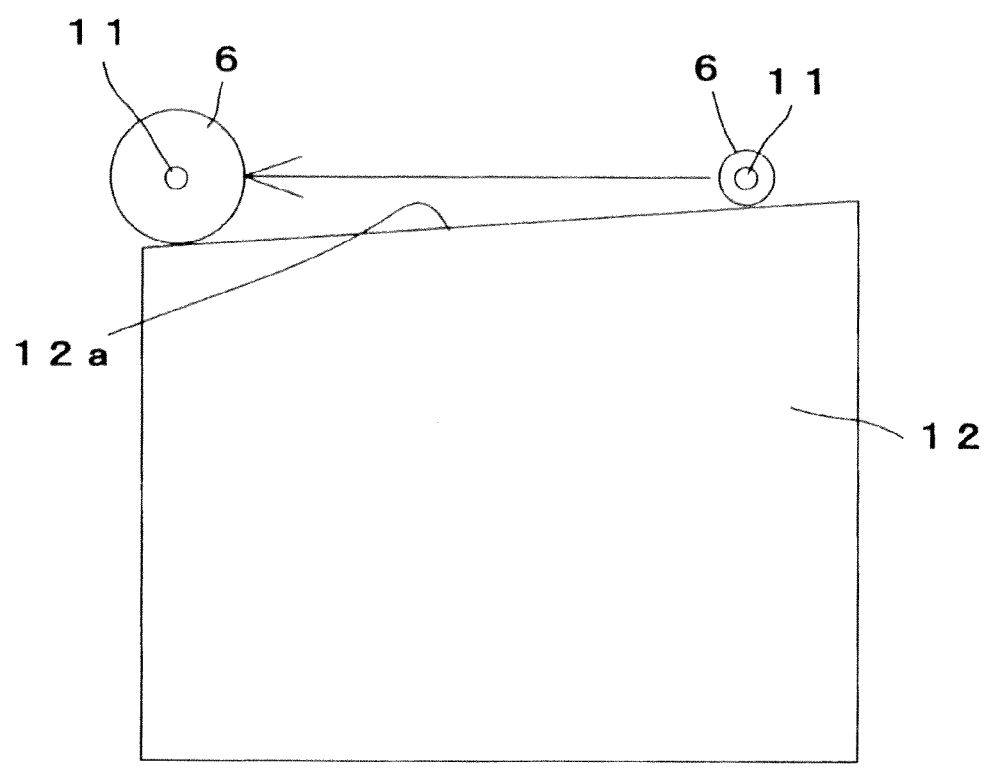
FIG. 13 illustrates an explanatory drawing of formation of a slope on the upper face of the mounting block.

Furthermore, as mentioned above, along with the winding of the tissue piece around the core rod 11, the diameter of the tissue piece gradually increases. Thereby, as shown in FIG. 13, if a slope gradually descending in the moving direction of the core rod 11 is formed on an upper face 12a of the mounting block 12, the position of the core rod 11 need not to be raised. In such a case, the core rod-attaching part 32 may be preferably horizontally moved at a constant height.

When a slope is not formed on the upper face 12a of the mounting block 12, a rising mechanism which gradually raises the core rod 11 in the moving direction should be used for the core rod-attaching part 32 or the movable table 40.

In relation to the core rod 11 used for winding of the tissue piece, a smaller diameter is preferable because a density of the wound tissue piece is increased. Specifically, the diameter may be 4 mm or less, preferably about 1 to 2 mm.

Furthermore, before the use of the core rod 11 for winding of the tissue piece, by the fact that the whole of the core rod 11 is soaked in the fused paraffin, a state is reached where the cylinder in the core rod 11 is filled with the paraffin, and the paraffin is coated throughout the outer wall.

In this way, deformation of the tissue piece can be prevented so as not to squash the core rod 11 in cutting, by the fact that the inner space of the core rod 11 is filled with the paraffin.

In addition, when the sheet-like tissue piece 8 is wound, its adhesiveness to the core rod 11 can be enhanced, by the fact that the periphery of the core rod 11 is coated with the paraffin. In this case, as the paraffin used for coating, paraffin having a melting-point temperature to the extent that the adhesiveness can be caused by the heater on the mounting block 12, or this paraffin blended with an adhesive material such as a butyl rubber may be used.

What is claimed is:

1. A device for forming tissue pieces for a tissue array comprising:
    a mounting block comprising an upper face on which a previously sliced sheet-like tissue piece is operable to be placed, the previously sliced tissue piece made by slicing a tissue block of a tissue in an embedding medium;
    a means for enabling peeling off of the tissue piece from the mounting block, said peeling means being provided on the upper face of the mounting block;
    a first heating unit operable to heat the sheet-like tissue piece placed on the mounting block;
    a core rod-attaching part operable to attach a core rod for winding the sheet-like tissue piece, being provided above the upper face of the mounting block;
    a motor coupled to the core rod-attaching part and operable to rotate a core rod attached to the core rod-attaching part around the shaft core of the core rod;
    a means for horizontally moving the core rod-attaching part relative to the upper face of the mounting block;
    a control unit which controls the motor and the horizontal moving means so that the core rod is horizontally moved by the horizontal moving means while rotating by the motor, such that a sheet-like tissue piece placed on the upper face of the mounting block is wound around the core rod into a cylindrical form;
    a second heating unit operable to heat a roll-shaped tissue piece rolled around the core rod in order to adapt it;
    a cooling unit operable to cool a roll-shaped tissue piece heated by the second heating unit; and
    a cutting unit operable to cut a roll-shaped tissue piece and the core rod cooled by the cooling unit, to form a cylindrical body of a predetermined length.

2. The device according to claim 1, wherein the peeling means comprises an embedding medium having a melting point lower than that the embedding medium of the sheet-like tissue piece.

3. The device according to claim 1, wherein the embedding medium is paraffin.

4. The device according to claim 1, wherein the peeling means comprises an upper face of the mounting block that is roughened.

5. The device according to claim 1, further comprising a plate operable to be positioned and detachable from the upper face of the mounting block, and wherein the peeling means is applied to an upper face of the plate.

6. The device according to claim 1, the device including means that press the core rod in a direction of the sheet-like tissue piece when the sheet-like tissue piece is wound around the core rod attached to said core rod-attaching part, and which can move following movement of the core rod by said horizontal moving means.

7. The device according to claim 1, wherein the mounting block slopes in a direction gradually being spaced apart from the core rod toward a moving direction of the core rod.

8. The device according to claim 1, wherein the core rod-attaching part is provided so that it can move in a direction gradually being spaced apart from the sheet-like tissue piece toward the moving direction of the core rod.

9. The device according to claim 1, wherein when the sheet-like tissue piece is wound around the core rod attached to said core rod-attaching part, the control unit performs control so that an amount of movement by the horizontal moving means is gradually increased and a rotation speed by the motor is gradually lowered.

10. The device according to claim 1, wherein the embedding medium is coated on the surface of said core rod.

* * * * *